United States Patent [19]
Senapathy

[11] Patent Number: 5,994,058
[45] Date of Patent: Nov. 30, 1999

[54] METHOD FOR CONTIGUOUS GENOME SEQUENCING

[75] Inventor: Periannan Senapathy, Wheaton, Ill.

[73] Assignee: Genome International Corporation, Madison, Wis.

[21] Appl. No.: 08/406,545

[22] Filed: Mar. 20, 1995

[51] Int. Cl.[6] .............................. C12Q 1/68; C07H 21/02; C12P 19/34; C12N 15/00
[52] U.S. Cl. ........................... 435/6; 536/23.1; 536/24.3; 935/76; 935/77; 935/78
[58] Field of Search ..................... 435/6, 91.2; 536/22.1, 536/23.1, 24.3; 935/76, 77, 78

[56] References Cited

U.S. PATENT DOCUMENTS

| | | | |
|---|---|---|---|
| 5,104,792 | 4/1992 | Silver et al. | 435/6 |
| 5,106,727 | 4/1992 | Hartley et al. | 435/6 |
| 5,108,892 | 4/1992 | Burke et al. | 435/6 |
| 5,407,799 | 4/1995 | Studier | 435/6 |
| 5,487,985 | 1/1996 | McClelland et al. | 435/91.2 |
| 5,487,993 | 1/1996 | Herrnstadt et al. | 435/172.3 |
| 5,508,169 | 4/1996 | Deugau | 435/6 |
| 5,731,171 | 3/1998 | Bohlander | 435/91.2 |

OTHER PUBLICATIONS

DNA Sequence—Journal DNA Sequencing and Mapping, vol. 2, issued 1992, P. Verhasselt et al., *DNA sequencing by a subcloning–walking strategy using a specific and semi–random primer in the polymerase chain reaction*, pp. 281–287.
Sarkar et al., DNA and Cell Biology 12 (7): 611–615 (1993).
Loh et al., Science 243: 217–220 (1988).
Volinia et al., CABIOS 5: 33–40 (1989).
Liu et al., Genomics 25: 674–681 (1995).
Kotler et al., PNAS 90: 4241–4245 (1993).
Caetano–Anollés et al., Mol. Gen. Genet. 235:157–165 (1992).
Nevinsky et al., Biochemistry 29:1200–1207 (1990).
Studier, F W., PNAS 86: 6971–6921 (1989).
Parker et al. Nucleic Acids Research 19(11):3055–3060.

*Primary Examiner*—W. Gary Jones
*Assistant Examiner*—Ethan Whisenant

[57] ABSTRACT

A new contiguous genome sequencing method is described which allows the contiguous sequencing of a very long DNA without need to be subcloned. It uses the basic PCR technique but circumvents the usual need of this technique for the knowledge two primers for contiguous sequencing, enabling the knowledge of only one primer sufficient. The present invention makes it possible to PCR amplify a DNA adjacent to a known sequence with which one primer can be made without the knowledge of the second primer binding site present in the unknown sequence. The present invention could thus be used to contiguously sequence a very long DNA such as that contained in a YAC clone or a cosmid clone, without the need for subcloning smaller fragments, using the standard PCR technique. It can also be used to sequence a whole chromosome or genome without any need to subclone it.

6 Claims, 5 Drawing Sheets

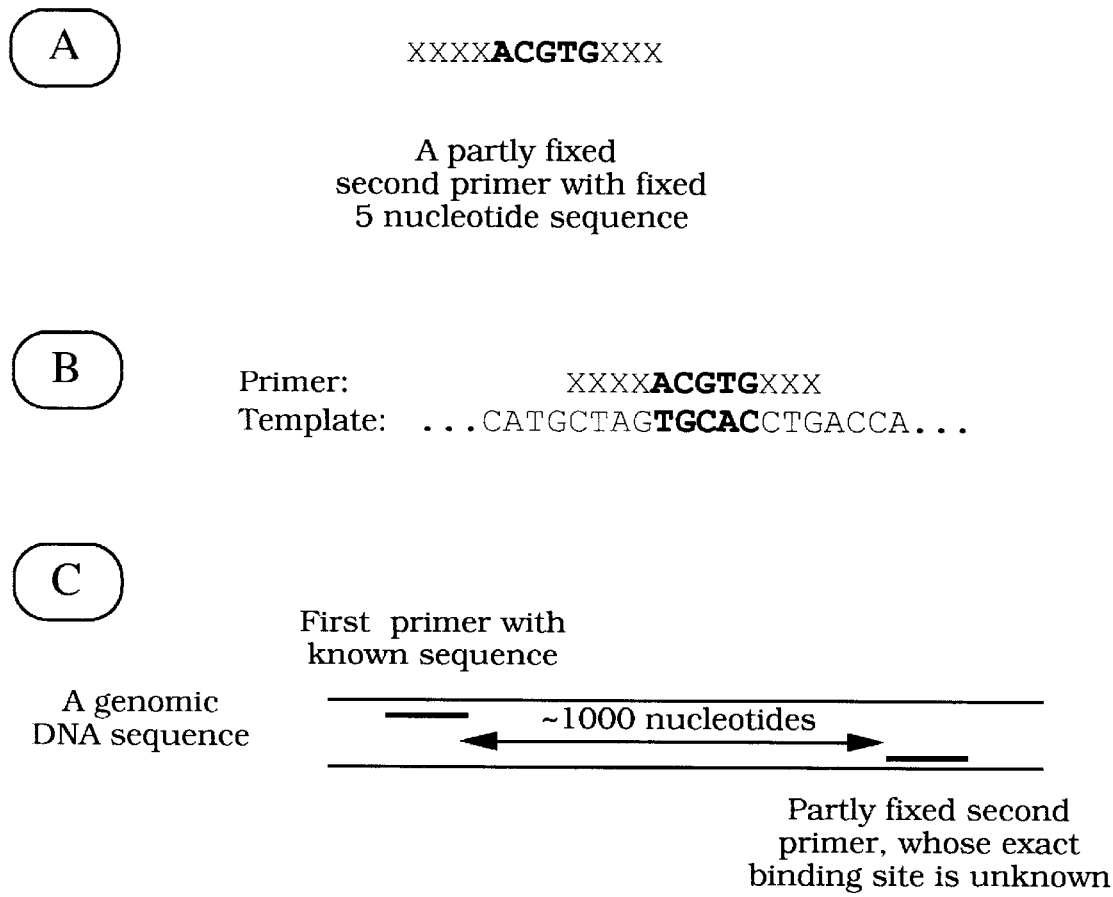

FIG. 1.

A) A partly random primer with a fixed sequence that is used as the second primer in the present invention. The length and composition of the fixed sequence and/or the random sequence (X's) and their positions within the primer, and the length of the primer itself can be adjusted to improve binding specificity and affinity, within the reaction conditions generally used in PCR protocols and DNA sequencing reactions.

B) The primer can bind to the template only at the sequence complementary to the fixed sequence in the primer.

C) This partly fixed second primer has a high specificity of binding at an ideal distance from the first known primer for PCR amplification and DNA sequencing.

Known template sequence, from which the first primer is prepared

An exact template sequence, located at an approx. distance of 1000 characters from the first primer, at which the partly fixed 5-nucleotide primer will bind

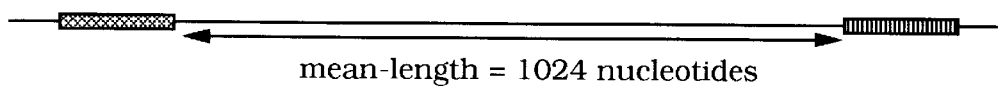

mean-length = 1024 nucleotides

FIG.2. Precise binding of the partly fixed second primer to a specific sequence, located at an unknown distance from the first primer, but within a specified range of distance which is highly suitable for DNA amplification by the PCR technique and DNA sequencing by the standard techniques.

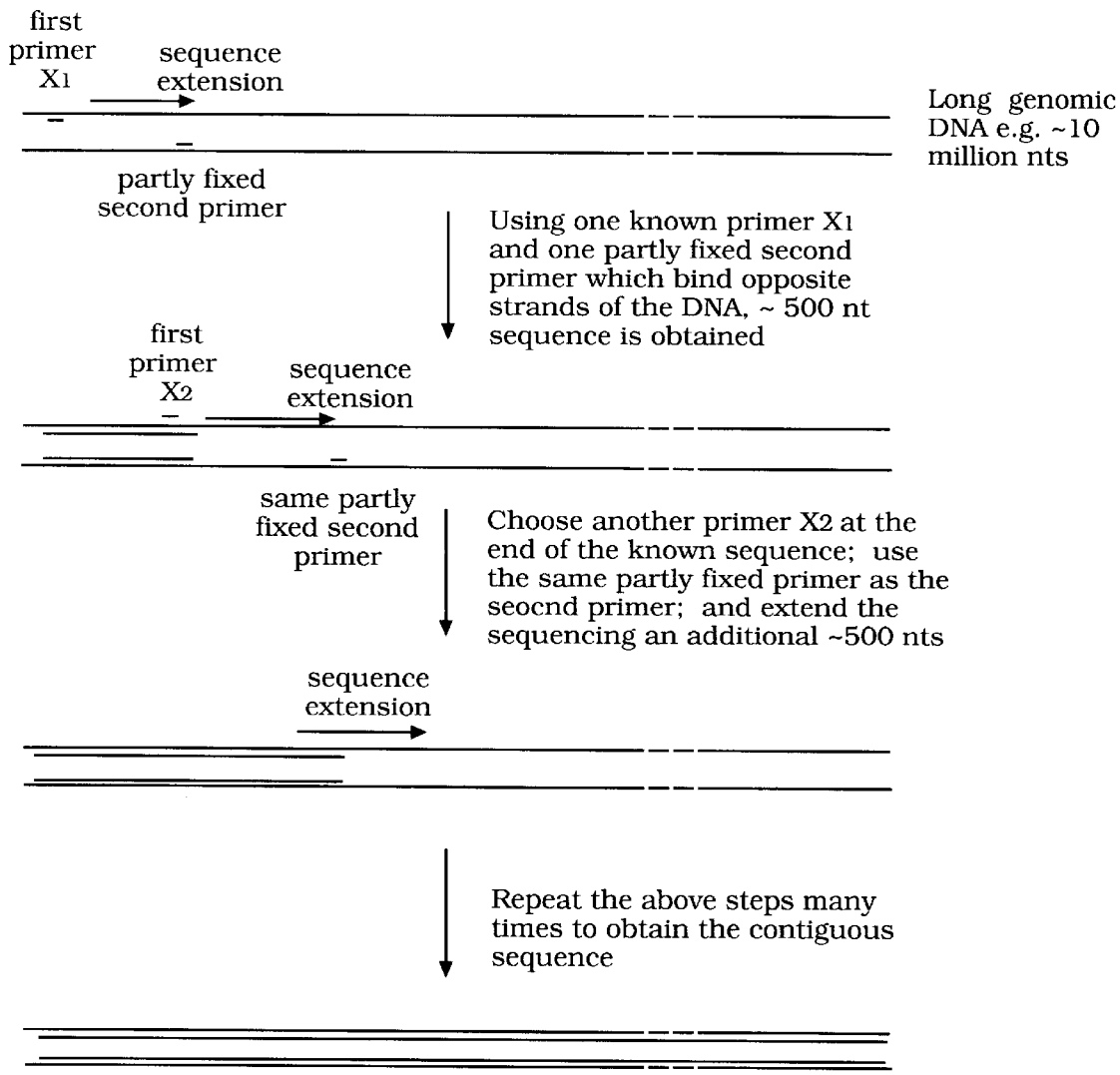
FIG. 3. Congituous genome-sequencing using a partly fixed primer as the second primer.

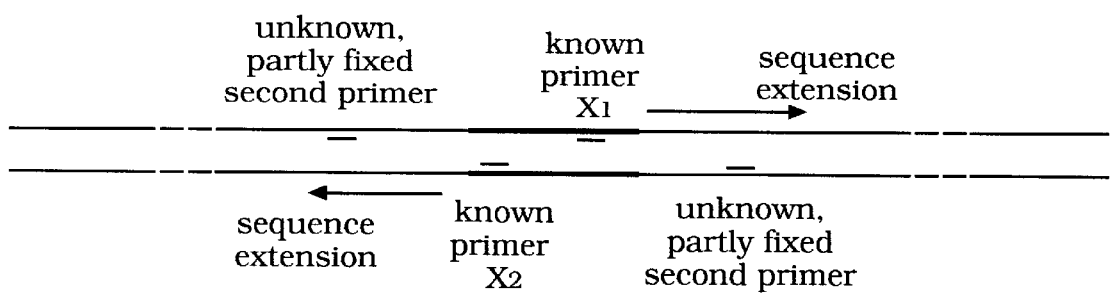
FIG. 4. Extension of DNA sequencing in both directions from a known sequence region (bold lines) in a very long DNA, using the same set of partly fixed second primers.

(A) ATCATGTAAGTAGGC

An arbitrary but exact primer sequence of 15 nucleotides length, which would probabilistically have approximately one binding site in a genome of about one billion nucleotides.

(B) 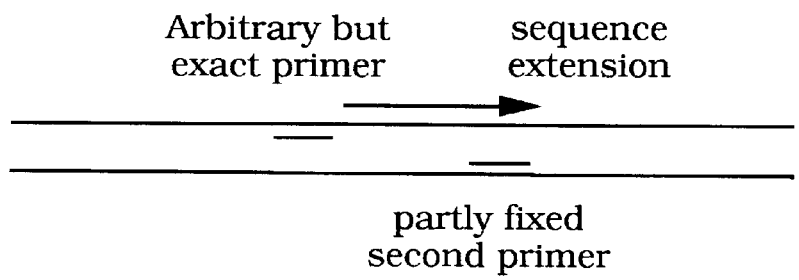

FIG. 5. Determining a DNA sequence from a long DNA of completely unknown sequence using an arbitrary but exact sequence primer and an unknown, partly fixed second primer.

METHOD FOR CONTIGUOUS GENOME SEQUENCING

BACKGROUND OF THE INVENTION

The present invention provides a method for contiguous sequencing of very long DNA using a modification of the standard PCR technique without the need for breaking down and subcloning the long DNA.

The PCR technique enables the amplification of DNA which lies between two regions of known sequence (K. B. Mullis et al., U.S. Pat. Nos. 4,683,202; 7/1987; 435/91; and 4,683,195, 7/1987; 435/6). Oligonucleotides complementary to these known sequences at both ends serve as "primers" in the PCR procedure. Double stranded target DNA is first melted to separate the DNA strands, and then oligonucleotide (oligo) primers complementary to the ends of the segment which is desired to be amplified are annealed to the template DNA. The oligos serve as primers for the synthesis of new complementary DNA strands, using a DNA polymerase enzyme and a process known as primer extension. The orientation of the primers with respect to one another is such that the 5' to 3' extension product from each primer contains, when extended far enough, the sequence which is complementary to the other oligo. Thus, each newly synthesized DNA strand becomes a template for synthesis of another DNA strand beginning with the other oligo as primer. Repeated cycles of melting, annealing of oligo primers, and primer extension lead to a (near) doubling, with each cycle, of DNA strands containing the sequence of the template beginning with the sequence of one oligo and ending with the sequence of the other oligo.

The key requirement for this exponential increase of template DNA is the two oligo primers complementary to the ends of the sequence desired to be amplified, and oriented such that their 3' extension products proceed toward each other. If the sequence at both ends of the segment to be amplified is not known, complementary oligos cannot be made and standard PCR cannot be performed. The object of the present invention is to overcome the need for sequence information at both ends of the segment to be amplified, i.e. to provide a method which allows PCR to be performed when sequence is known for only a single region, and to provide a method for the contiguous sequencing of a very long DNA without the need for subcloning of the DNA.

DNA sequencing is a technique by which the four DNA nucleotides (characters) in a linear DNA sequence is ordered by chemical and biochemical means. There are two techniques: 1) the chemical method of Maxam and Gilbert (A. M. Maxam, and W. Gilbert, "A new method of sequencing DNA." *Proceedings of the National Academy of Sciences, USA*, 74:560–564 (1977)), and the enzymatic method of Sanger and colleagues (F. Sanger, S. Nicklen, and A. R. Coulson, "DNA sequencing with chain-terminating inhibitors." 74:5463–5467 (1977)). In the chemical method, the DNA strand is isotropically labeled on one end, broken down into smaller fragments at sequence locations ending with a particular nucleotide (A, T, C, or G) by chemical means, and the fragments ordered based on this information. The four nucleotide-specific reaction products are resolved on a polyacrylamide gel, and the auto radiographic image of the gel is examined to infer the DNA sequence.

In the enzymatic method, the following basic steps are involved:
(i) annealing an oligonucleotide primer to a suitable single or denatured double stranded DNA template; (ii) extending the primer with DNA polymerase in four separate reactions, each containing one α-labeled dNTP or ddNTP (alternatively a labeled primer can be used), a mixture of unlabeled dNTPs, and one chain-terminating dideoxynucleoside-5'-triphosphate (ddNTP); (iii) resolving the four sets of reaction products on a high resolution polyacrylamide-urea gel; and (iv) producing an auto radiographic image of the gel that can be examined to infer the DNA sequence. Alternatively, fluorescently labeled primers or nucleotides can be used to identify the reaction products. Known dideoxy sequencing methods utilize a DNA polymerase such as the Klenow fragment of *E. coli* DNA polymerase, reverse transcriptase, a modified T7 DNA polymerase, or the Taq polymerase.

The PCR amplification procedure has been used to sequence the DNA being amplified (e.g. "Introduction to the AmpliTaq Cycle Sequencing Kit Protocol", a booklet from Perkin Elmer Cetus Corporation). The DNA could be first amplified and then it could be sequenced using the two conventional DNA sequencing techniques. Modified methods for sequencing PCR-amplified DNA have also been developed (e.g. Bevan et al., "Sequencing of PCR-Amplified DNA" *PCR Meth. App.* 4:222 (1992)). However, amplifying and sequencing using the PCR procedure requires that the sequences at the ends of the DNA (the two primer sequences) be known in advance. Thus, this procedure is limited in utility, and cannot be extended to contiguously sequence a long DNA strand. If the knowledge of only one primer is sufficient without anything known about the other primer, it would be greatly advantageous for sequencing very long DNA molecules using the PCR procedure. It would then be possible to use such a method for contiguously sequencing a long genomic DNA without the need for subcloning it into smaller fragments, and knowing only the very first, beginning primer in the whole long DNA.

In the currently existing methods for sequencing very long DNA of millions of nucleotides, the DNA is fragmented into smaller, overlapping fragments, and sub-cloned to produce numerous clones containing overlapping DNA sequences. These clones are sequenced randomly and the sequences assembled by "overlap sequence-matching" to produce the contiguous sequence. In this shot-gun sequencing method, approx. ten times more sequencing than the length of the DNA being sequenced is required to assemble the contiguous sequence. In the "directed" sequencing method, the linear order of the DNA clones has to be first determined by "physical mapping" of the clones.

There exists a contiguous DNA sequencing method called the "primer-walking" method using the Sanger's DNA polymerase enzymatic sequencing procedure. In this method, however, the DNA copying has to occur always from the template DNA during DNA sequencing. In contrast, in the PCR procedure, the target DNA amplified in the first rounds from the original input template DNA will function as the template DNA in subsequent cycles of amplification. After a certain cycles of amplification, the DNA sequencing reaction will be started by adding the sequencing "cocktail". Thus in the PCR reaction, only one copy of template DNA is theoretically sufficient to amplify into millions of copies, and therefore a very little genomic (or template) DNA is sufficient for sequencing. The advantage of DNA amplification that exists in PCR is lacking in the conventional Sanger procedure. Thus, this primer-walking method will require a larger amount of template DNA compared to the PCR sequencing method. Also, because the long DNA has a tendency to re-anneal back to duplex DNA, the sequencing gel pattern may not be as clean as in a PCR procedure, when a very long DNA is being sequenced. This may limit the length of the DNA, that could be contiguously sequenced without breaking the DNA, using the primer-walking procedure. The PCR method also enables the reduction of non-specific binding of the primers to the template DNA because the enzymes used in these protocols function at high-temperatures, and thus allow "stringent" reaction conditions to be used to improve sequencing.

The present method of contiguous DNA sequencing using the basic PCR technique has thus many advantages over the primer walking method. Also, so far no method exists for contiguously sequencing a very long DNA using PCR technique. The present invention thus offers a unique and very advantageous procedure for contiguous DNA sequencing.

SUMMARY OF THE INVENTION

The present invention enables the amplification of a DNA stretch using the PCR procedure with the knowledge of only one primer. Using this basic method, the present invention describes a procedure by which a very long DNA of the order of millions of nucleotides can be sequenced contiguously, without the need for fragmenting and sub-cloning the DNA. In this method, the general PCR technique is used, but the knowledge of only one primer is sufficient, and the knowledge of the other primer is derived from the statistics of the distributions of oligonucleotide sequences of specified lengths.

Present DNA sequencing methods using the separation of DNA fragments on a gel has a limitation of resolving the products of length up to about 1000 nucleotides. Thus, in a single step, the sequence of a DNA fragment up to a length of only about 1000 nucleotides can be obtained by the two conventional DNA sequencing methods. A DNA sequence of a few nucleotides up to many thousand nucleotides can be amplified by the PCR procedure. Thus the PCR procedure can be combined with the DNA sequencing procedure successfully.

A primer is usually of length twelve nucleotides and longer. Let the sequence of one primer is known in a long DNA sequence from which the DNA sequence is to be worked out. From this primer sequence, a specific sequence of four nucleotides occurs statistically at an average distance of 256 nucleotides. It has been worked out by Senapathy that a particular sequence of four characters would occur anywhere from zero distance up to about 1500 characters with a 99.9% probability (P. Senapathy, "Distribution and repetition of sequence elements in eukaryotic DNA: New insights by computer aided statistical analysis," *Molecular Genetics (Life Sciences Advances)*, 7:53–65 (1988)). The mean distance for such an occurrence is 256 characters and the median is 180 characters. Similarly, a 5 nucleotide long specific sequence will occur at a mean distance of 1024 characters, with 99.99% of them occurring within 6000 characters from the first primer. The median distance for the occurrence of a 5-nucleotide specific sequence is ~730 nucleotides. Similarly, a particular 6 nucleotide long sequence will occur at a mean distance of 4096 nucleotides and a median distance of ~2800 nucleotides. A primer of known length, say length 14 can be prepared with a known sequence of 6 characters and the rest of the sequence being random in sequence. It means that any of the four nucleotides can occur at the "random" sequence locations. With a fixed 5, 6 or 7 nucleotide sequence within the second primer, a primer of length 12–18 can be prepared with high specificity of binding.

Such a partially non-random primer (hereafter called the partly fixed primer, or partly non-random primer, meaning that part of its sequence is fixed) can "anneal" to only the sequence at which the fixed sequence exists. That is, from the first primer, the partly fixed primer will bind at an average distance of 1024 characters (for a fixed five nucleotide characters). This primer will bind specifically only at the location of the occurrence of the particular five nucleotide sequence with respect to the first primer. The average distance between the first primer and the second non-random primer is ideal for DNA amplification and DNA sequencing. In this situation, the first primer is labeled. Thus, although there would be many locations in the long DNA molecule at which the non-random primer can bind, it would not affect the DNA sequencing because it is dependent only upon the labeled primer.

Although the partly fixed second primer has a random sequence component in it, a sub-population of the primer molecules will have the exact sequence that would bind with the exact target sequence. The proportion of the molecules with exact sequence that would bind with the exact target sequence will vary depending on the number of random characters in the partly fixed second primer. For example, in a second primer 11 nucleotides long with 6 characters fixed and 5 characters random, one in ~1000 molecules will have the exact sequence complementary to the target sequence on the template. By increasing the concentration of the partly fixed second primer appropriately, a comfortable level of PCR amplification required for sequencing can be achieved. When primer concentration is increased, it requires an increase in the concentration of Magnesium, which is required for the function of the polymerase enzyme. The excess primers (and "primer-dimers" formed due to excess of primers) can be removed after amplification reaction by a gel-purification step.

Any non-specific binding by any population of the second primers to non-target sequences could be avoided by adjusting (increasing) the temperature of re-annealing appropriately during DNA amplification. It is well known that the change of even one nucleotide due to point-mutation in some cancer genes can be detected by DNA-hybridization. This technique is routinely used for diagnosing particular cancer genes (e.g. John Lyons, "Analysis of ras gene point mutations by PCR and oligonucleotide hybridization," in *PCR Protocols: A guide to methods and applications*, edited by Michael A Innis et al., (1990), Academic Press, New York). This is done by adjusting the "re-annealing" or "melting-temperature", and fine-tuning the reaction conditions. Thus the binding of non-specific sequences even with just one nucleotide difference compared to the target binding-site in the template sequence can be avoided.

It should also be noted that non-specific binding sites for the partly fixed second primers could be expected to occur statistically on a long genomic DNA at many places other than the target site which is close to the first primer. Amplification of non-specific DNA between these primer binding sites that could occur on opposite strands of the template DNA could happen. However, this would not affect the objective of the present invention of specific DNA sequencing of the target sequence. Because only the first primer is labeled radioactivity or fluorescently, only the reaction products of the target DNA will be visualized on the sequencing gel pattern. The presence of such non-specific amplification products in the reaction mixture will also not affect the DNA sequencing reaction.

Amplification of DNA will occur not only between the first primer and the partly fixed second primer that occurs closest downstream from the first primer, but also between the first primer and one or two subsequently occurring second primers, depending upon the distance at which they occur. However, these amplification products will all start from the first primer and will proceed up to these second primers. Since the DNA sequencing products are visualized by labeling the first primer, and since the DNA synthesis during the sequencing reaction proceeds from the first primer, the presence of two or three amplification products that start from the first primer will not affect the DNA sequencing products and their visualization on gels. At the most, the intensity of the bands that are subsets of different amplification products will vary slightly on the gel, but not affect the gel pattern. In fact, it is expected that this phenomenon will enable the sequencing of a longer DNA strand where the closest downstream primer is too close to the first primer—thereby avoiding the need for sequencing from the first primer again using another partly fixed second primer.

The minimum length of primer for highly specific amplification between primers on a template DNA is usually considered to be about 15 nucleotides. However, in the present invention, this length can be reduced by increasing the G/C content of the fixed sequence to 12–14 nucleotides.

In essence, the basic procedure of the present invention is fully viable and feasible, and any non-specificity can be avoided by fine-tuning the reaction conditions such as adjusting the annealing temperature and reaction temperature during amplification, and/or adjusting the length and G/C content of the primers, which are routinely done in the standard PCR amplification protocol.

The primary advantage of the present invention is to provide an extremely specific second primer that would bind precisely to a sequence at an appropriate distance from the first primer resulting in the ability to sequence a DNA without the prior knowledge of the second primer. From the newly worked out DNA sequence, a primer sequence can be made complementary to a sequence located close to the downstream end. This can be used as the first primer in the next DNA amplification-sequencing reaction, and the unknown sequence downstream from it can be obtained by again using the same partly fixed primer that was used in the first round of sequencing as the second primer. Thus, knowing only one short sequence in a contiguously long DNA molecule, the entire sequence can be worked out using the present invention.

When the length of the fixed sequence in the partly fixed second primer is increased in the present invention, the distance from the first primer at which the second primer will bind on the template will also be correspondingly increased. For a 6 nucleotide fixed sequence, the median length of DNA amplified will be ~2800 nucleotides (mean 4096 nucleotides), and for a 7 nucleotide fixed sequence, the median length of amplified DNA will be ~11,000 nucleotides (mean=~16,000 nucleotides). However, even if the length of amplified DNA is several thousand nucleotides, still this DNA can be used in DNA sequencing procedures. Furthermore, the present invention can be used to amplify a DNA of length which is limited only by the inherent ability of PCR amplification. A technique known as "long PCR" is used to amplify long DNA sequences (Kainz et at., "In vitro amplification of DNA Fragments >10 kb," *Anal Biochem.*, 202:46 (1992); Ponce & Micol, "PCR amplification of long DNA fragments" *Nucleic Acids Research*, 20:623 (1992)).

Existing genome sequencing methods employ the breaking down of a very long genomic DNA into many small fragments, sub-cloning them, sequencing them, and then assembling the sequence of the long DNA. Typically, a genomic DNA is broken down and cloned into overlapping fragments of approx. one million nucleotides in "YAC" (Yeast Artificial Chromosome) clones, each YAC clone is again fragmented and sub-cloned into overlapping fragments of ~25,000 nucleotides in "cosmid" clones, and each cosmid clone in turn sub-cloned into overlapping fragments of ~1000 nucleotides in "M13 phage" or "plasmid" clones. These are sequenced randomly to assemble the larger sequences in the hierarchy. The present invention circumvents the need for breaking down and sub-cloning steps, making it greatly advantageous for contiguously sequencing long genomic DNA.

Extending the above invention, another invention is presented here. This extended invention would enable the sequencing of ~500 nucleotide long sequence somewhere within a given long DNA with no prior information of any sequence at all within the long DNA. The probability that any specific primer of length 10 nucleotides would occur somewhere in a DNA of about one million nucleotides is approximately 1. The probability that any primer of length 15 nucleotides occur somewhere in a genome of about one billion nucleotides is approximately 1. Thus, use of any exact primer of about 15 nucleotide sequence on a genomic DNA in the present invention as the first primer, and the use of the second partly fixed primer will enable the sequencing of the DNA sequence bracketed by the two primers somewhere in the genome. Thus, this procedure can be used to obtain an exact sequence of about 500 characters somewhere from a genome without the prior knowledge of any of its sequence at all. Thus, by using many different primers with arbitrary but exact sequences, one can obtain many ~500-nucleotide sequences at random locations within a genome. Using these sequences as the starting points for contiguous genome sequencing in the present invention, the whole genomic sequence can be closed and completed. Thus an advantage of the present invention is that without any prior knowledge of any sequence in a genome, the whole sequence of a genome can be obtained.

It must be noted that every 15-nucleotide arbitrary primer may not always have a complementary sequence in a genome (of ~one billion nucleotides long). However, most often it would be present and would be useful in performing the above-mentioned sequencing. In some cases, there may be more than one occurrence of the primer sequence in the genome, and so may not be useful in obtaining the sequence. However, the frequency of successful single-hits can be extremely high (~90%) and can be further refined by using an appropriate length of the arbitrary primer. For genomes (or long DNAs) that are shorter than a billion nucleotides, shorter exact sequences in the first primers (say 10 characters) could be used, and the rest could be random or "degenerate" nucleotides. While this primer will still bind at the sequence complementary to the exact sequence, the longer primer will aid in avoiding non-specific DNA amplification. The length of the first primer can thus be increased using degenerate nucleotides at the ends to a desired extent, without affecting any specificity. Once a sequence is known in an unknown genomic DNA, then the present method can be performed to extend a contiguous sequence in both directions of the DNA from this starting point.

The present invention can also be useful to amplify the DNA between the first primer and the partly fixed second primer, with an aim to using this amplified DNA for purposes other than DNA sequencing, such as cloning. Although there would be sufficient quantity of the target specific amplified DNA in the reaction products, the reaction products will, however, contain the population of non-specific DNA amplified between the non-specifically occurring second primer binding sites on opposite strands. However, by introducing a purification step from this reaction mixture, such as using an immobilized column containing only the first primer, the amplified target DNA can be purified and used for any other purposes.

UTILITY OF THE INVENTION

The present invention enables the amplification of a DNA adjacent to a known sequence using the PCR, without the knowledge of the sequence for a second primer.

The present primary invention provides a new method for sequencing a contiguously very long DNA sequence using the PCR technique, thereby enabling contiguous genomic sequencing. It will avoid the need for mapping or sub-cloning of shorter DNA fragments from haploid genomes such as the bacterial genomes. This method can be used on very large DNA inserts into vectors such as the YAC. Thus, diploid genomes can be sequenced without any further need to sub-clone from the YAC clones. The cloned inserts can be of any length, of several million nucleotides. Alternatively, wherever purified chromosomes are available, this method can be directly applied to sequence the whole chromosome without any need to fragment the chromosome or obtain YAC clones from the chromosome. This method can also be used on whole unpurified genomes with appropriate modifications to account for the allelic variations of the two alleles present on the two chromosomes. In essence, using the method of the present invention, one can generate contiguous genomic sequence information in a manner not possible with any other known protocol using PCR.

The present invention can find applications in many fields, for instance, medical, diagnostic, forensic, genetics, biotechnology, and genome research. It should be noted that this technique would be applicable in many other fields and instances, and such applications would be discernible by people of ordinary skills in the respective fields.

The extended invention that enables the sequencing of an unknown region of very long DNA (e.g. genomic DNA) of totally unknown sequence would also find many applications in biology and medicine. For instance, it can be used to physically "map" a chromosome or genome. It would, for example, enable the production of an inventory of many ~500 nucleotide long sequences and the exact primer associated with each of them. This method would also enable the cloning of the amplified DNA sequences from arbitrary regions from a genomic DNA without the need for breaking down the DNA. Using appropriately longer partly fixed primers (as the second primers), very long DNA pieces (several kilobases long) could be amplified and cloned by using this method.

BRIEF DESCRIPTION OF THE DRAWINGS

FIGS. 1(A–C) shows that the partly fixed second primer can bind only to the sequence locations in the "template" DNA (the DNA to be sequenced) containing the complementary sequence to the specific fixed sequence. The fixed sequence in the second primer is long enough and the rest of the random sequence is short enough that the random binding of this primer to any other sequence location in the template DNA is automatically precluded. This ensures that the second primer will bind extremely specifically to the sequence complementary to the fixed four or five nucleotide sequence used in the second primer, under the reaction conditions generally used in the PCR protocols. It should be noted that any sequence of five nucleotide length could be used in the fixed primer and the rest being random sequence. This is because, statistically, any of these sequences would occur at an appropriate average distance from the first primer. This is one of the primary advantages offered by the new invention. The advantage of this method stems from the chance occurrences of fixed sequences of particular length appropriate for DNA sequencing by the PCR technique. The statistical distribution of sequences of particular lengths has been worked out by Senapathy. Senapathy has also shown that natural DNA is essentially random in DNA sequence (P. Senapathy, "Origin of Eukaryotic Introns: A hypothesis, based on codon distribution statistics in genes, and its implications," *Proceedings of the National Academy of Sciences*, USA. 83:2133–2137 (1986)). The fixed sequence in the partly fixed second primer can be present at either ends of the primer or anywhere within the primer. Also, the fixed sequence within the second primer can be of any length, 4, 5, 6, or longer oligonucleotides. Furthermore, the fixed sequence can be split into 2 or 3 shorter fixed sequences at various positions within the second primer, still giving the same statistical result and binding property.

FIG. 2 shows that the mean-length between the first primer and the partly fixed second primer is appropriate for DNA sequencing using the PCR technique. For instance, the median length at which the sequence complementary to the second primer will be found is 730 nucleotides, which is ideal for DNA sequencing. This means, although the second primer will occur anywhere from zero distance up to about 6000 nucleotides, 50% of the time it will occur at around 730 nucleotides. Thus, by using two different fixed five nucleotide sequences in two different second primers, the chance that the DNA sequence of appropriate length can be sequenced is achieved with a probability of 99.9%. In the actual protocol, the length of a DNA sequence obtained in the new method would be known only when the results of a sequencing experiment is obtained. At this stage, if sufficient length of sequence is not obtained, then another second primer with a different fixed sequence could be used. With only a few different fixed five or six nucleotide sequences in the second primers, contiguous genomic sequencing can be systematically carried out. This means one needs to prepare only a few, say ten different second primers for sequencing the whole genome, which can be done at relatively very low expense and in bulk at one time at the start of sequencing a genome.

FIG. 3 shows how the partly fixed primer is used as the unknown second primer in contiguous genome sequencing. In a long template DNA, a sequence at the starting position should be known from which a first primer could be made. From this point, a stretch of the DNA sequence can be obtained using the new method. An appropriate sequence is selected from the downstream end of this sequence for making a primer that will be used as the first known primer for extending the sequencing. Using this primer and the same partly fixed primer as the unknown second primer, the sequence is extended further. This procedure is continuously repeated until the end of the sequence is reached.

FIG. 4 is a schematic indicating that the present invention enables the sequencing of a very long DNA in both directions from a starting known sequence location. From a known short sequence of only about a hundred nucleotides, two primers can be prepared such that they bind to opposite strands of the DNA. Using each of these known primers and the same second, partly fixed primer, sequencing can be extended in opposite directions on the DNA from the starting location.

FIGS. 5(A–B) describes the method to obtain the sequence of about 500 nucleotides from a genome or a very long DNA, from which absolutely no sequence information is available. Depending on the length of the very long DNA (or the genome), a primer with an arbitrary but exact sequence is designed such that it would have approximately one binding site in the long DNA. This primer binding site will also have a site close to it (at an average distance of about 800 nucleotides) that will bind with the second, partly fixed (5 nucleotide) sequence primer. With the first primer radiolabeled or fluorescent labeled, the DNA sequence between the two primers can be obtained by performing PCR amplification and DNA sequencing. It should be noted that this is possible only because the unknown second, partly fixed primer will almost certainly occur within a distance ideal for PCR amplification and DNA sequencing from the first primer—no matter where in the long DNA the first primer occurs.

DETAILED DESCRIPTION OF THE INVENTION

The above and various other objects and advantages of the present invention are achieved by a method comprising:

a) synthesizing a partly fixed primer, with 4, 5, 6 nucleotide, or longer sequence characters fixed within it. The fixed sequence can be any sequence, with some preferred sequences such as those containing many G–C pairs that increases binding affinity. The fixed position within the primer can be anywhere, with some preferred positions;

b) taking a very long genomic DNA, either uncloned or a cloned large insert such as the YAC or cosmid in which a short sequence of about 20 characters somewhere within the DNA is known;

c) synthesizing a primer from the sequence known from the DNA in step b;

d) radiolabeling the primer in step c;

e) annealing the primers (from step a, and step d or step g as appropriate) to the DNA in step b, and amplifying the DNA between the attached primers;

f) performing DNA sequencing of the amplified DNA by the chemical degradation method of Maxam and Gilbert, or carrying out DNA sequencing by the Sanger method, or by modified PCR-sequencing method;

g) after obtaining the DNA sequence from step f, selecting an appropriate first primer towards the 3' end of the sequence, synthesizing it, and radiolabeling it;

h) repeating the steps e through g with the two primers (the same partly fixed unknown primer as the second primer and the newly synthesized primer from step g as the first primer);

i) if the sequence obtained in step f is too short to be of value, using another partly fixed primer with a different fixed sequence and the same first primer to obtain a longer DNA sequence.

Unless defined otherwise, all technical and scientific terms used herein have the same meaning as commonly understood by one of ordinary skill in the art to which this invention belongs. All publications mentioned hereunder are incorporated herein by reference. Unless mentioned otherwise, the techniques employed herein are standard methodologies well known to one of ordinary skill in the art.

The partly fixed primer used to perform DNA amplification and sequencing are, of course, not limited to those described under the examples. Further modification in the method may be made by varying the length, content and position of the fixed sequence and the length of the random sequence. Additional obvious modifications include using different DNA polymerases and altering the reaction conditions of DNA amplification and DNA sequencing. Furthermore, the basic technique can be used for sequencing RNA using appropriate enzymes.

Instead of preparing the first primer completely, it can also be prepared as follows. Two or three shorter oligonucleotides that would comprise the complete primer could be ligated, by joining end-to-end after annealing to the template DNA, as described under another patent (Helmut Blocker, U.S. Pat. No. 5,114,839, 435/6, 5/1992) or as described in the publication (L. E. Kotler, et al., *Proceedings of the National Academy of Science, USA*, 90:4241–4245 (1993)). Alternatively, it can be synthesized using the single-stranded DNA binding protein, the subject of another invention (J. Kieleczawa, et al., *Science*, 258:1787–1791 (1992)). One of such procedures, or an improved version thereof, can be used to make the first primer in the present invention. All in all, the first primer need not be synthesized at every PCR reaction while contiguously sequencing a long DNA, and can be directly constructed from an oligonucleotide bank. Based on the present invention, the second primer also can be chosen from a set of only a few pre-prepared primers. This enables the direct automation of sequencing the whole long DNA by incorporating the primer elements into the series of sequential PCR reactions.

An advantage of the present invention is that from a known sequence in a very long DNA, sequencing can be performed in both directions on the DNA. Two first primers can be prepared, one on each strand, running in the opposite directions, and the sequence can be extended on both directions until the two very ends of the long DNA are reached by the present invention, using a small set of pre-prepared partly fixed second primers.

One of the major advantages of the present invention is that it is highly amenable to various kinds of automation. Instead of radiolabeling the first known primer, it can be fluorescently labeled, and with this the DNA sequencing can be performed in an automated procedure on machines such as that marketed by the Applied Biosystems ("373 DNA Sequencer: Automated sequencing, sizing, and quantitation", a pamphlet from the Applied Biosystems, A Division of Perkin-Elmer Corporation (1994)). In the present invention there is no need to newly synthesize any primers to sequence a very long DNA. Thus, with the pre-prepared set of partly fixed second primers, an oligonucleotide bank for the synthesis of the first primer, and a large supply of the template genomic DNA (or any long DNA), the sequencing of the whole long DNA can be automated using robots almost without any human intervention, except for changing the sequencing gels.

The following processes can be computer controlled: 1) the selection of the appropriate sequence for constructing the first primer close to the 3' end of the newly worked out sequence, 2) determining whether the sequence obtained is too short and selection of a different partly fixed second primer, 3) assembling the contiguous DNA sequences from the various lanes and various gels and appending to a database, and other such processes. Thus the present invention enables the construction of a fully automated contiguous DNA sequencing system. Any such automations are obvious modifications to the present invention.

The present invention is not limited to only unknown genomic DNA, and can be used to sequence any DNA under any situations. DNAs or RNAs of many different origins (e.g. viral, cDNA, mRNA) can be sequenced not only limited to research or information gathering purposes, but also to other purposes such as disease diagnosis and treatment, DNA testing, and forensic applications.

It is understood that the examples and embodiments described herein are for illustrative purposes only and that various modifications or changes in light thereof will be suggested to persons skilled in the art and are to be included within the spirit and purview of this application and scope of the appended claims.

It should be noted that any kit or process used for research, diagnostic, forensic, treatment, production or other purposes that uses the present invention is covered under these claims. Furthermore, the various sequences of the partly fixed second primers that can be used in the present invention are covered under this patent. Thus, any kit or process that uses this method and/or the DNA strands with the sequences that would comprise the partly fixed second primers will also be covered under this.

In addition to contiguous DNA sequencing, the present invention will cover the amplification of the DNA strands that are bounded between the known primer and the partly fixed second primer (either from claim 1 or from claim 2). The DNA amplification can also be performed for long DNA strands using the long PCR amplification protocols.

What is claimed is:

1. A method for amplifying by the polymerase chain reaction (PCR) a portion of a target nucleic acid sequence comprising the following steps:

a. providing a first primer wherein the first primer consists of a sequence fully complementary to a first primer binding site on said target nucleic acid sequence;

b. providing a second primer wherein said second primer consists of about 12–16 nucleotides of which 1–10 nucleotides anywhere within it are of fixed sequence, while the remaining nucleotides of the second primer are of random sequence, wherein the second primer is fully complementary to a second primer binding site; and c. performing PCR amplification using the primers of (a) and (b) and said target nucleic acid to effect the amplification of a portion of said target nucleic acid, wherein said amplification is under conditions of sufficient stringency so that specific amplification occurs.

2. The method of claim 1 further comprising sequencing the amplification product of step (c) thereby determining the sequence of a portion of said target nucleic acid sequence.

3. The method of claim 1 wherein the target nucleic acid is DNA.

4. The method of claim 1 wherein the target nucleic acid is RNA.

5. The method of claim 2 wherein the target nucleic acid is DNA.

6. The method of claim 2 wherein the target nucleic acid is RNA.

* * * * *